United States Patent [19]

Daluge

[11] Patent Number: 5,089,500

[45] Date of Patent: Feb. 18, 1992

[54] THERAPEUTIC NUCLEOSIDES

[75] Inventor: Susan M. Daluge, Chapel Hill, N.C.

[73] Assignee: Burroughs Wellcome Co., Research Triangle Park, N.C.

[21] Appl. No.: 697,260

[22] Filed: May 8, 1991

Related U.S. Application Data

[63] Continuation of Ser. No. 455,201, Dec. 22, 1989, Pat. No. 5,034,394, which is a continuation of Ser. No. 371,870, Jun. 26, 1989, abandoned.

[30] Foreign Application Priority Data

Jun. 27, 1988 [GB] United Kingdom ................. 8815265

[51] Int. Cl.$^5$ .................... A61K 31/52; C07D 473/30; C07D 473/32
[52] U.S. Cl. .................................... 514/261; 514/80; 514/81; 544/244; 544/277
[58] Field of Search ........................... 544/277, 244 P; 514/261, 80, 81

[56] References Cited

U.S. PATENT DOCUMENTS

| | | | |
|---|---|---|---|
| 4,605,659 | 8/1986 | Verheyden et al. | 544/277 |
| 4,931,559 | 6/1990 | Vince et al. | 544/276 |
| 4,950,758 | 8/1990 | Vince et al. | 544/276 |
| 4,954,504 | 9/1990 | Chen et al. | 544/276 |
| 4,968,674 | 11/1990 | Taniyama et al. | 544/276 |

FOREIGN PATENT DOCUMENTS

| | | |
|---|---|---|
| A-28671/89 | 7/1989 | Australia . |
| 0236935A3 | 9/1987 | European Pat. Off. . |
| 0236935A2 | 9/1987 | European Pat. Off. . |
| 0325460A1 | 7/1989 | European Pat. Off. . |
| 0346132A1 | 12/1989 | European Pat. Off. . |
| 0349242A2 | 1/1990 | European Pat. Off. . |
| 0424064A1 | 1/1990 | European Pat. Off. . |
| 62177234 | 1/1989 | Japan . |
| 2179349A | 3/1987 | United Kingdom . |
| 2217320A | 10/1989 | United Kingdom . |

OTHER PUBLICATIONS

Yoshikawa, et al., Bulletin Chem. Soc., Japan, vol. 42, No. 12, 1969, pp. 3505-3508, Studies of Phosphorylation, III. Selective Phosphorylation of Unprotected Nucleosides.
Hoard, et al., J. Amer. Chem. Soc., vol. 87, No. 8, Apr. 20, 1965, pp. 1785-1788, Conversion of Mono- and Oligodeoxyribonucleotides of 5'-Triphosphates.
Shuto et al., Chem. Pharm. Bulletin, vol. 36, No. 12, 1988, pp. 5020-5023 Phospholipase D-Catalyzed Trans-Alkylphosphorylation: A Facile One-Step Synthesis of Nucleoside 5'-Alkylphosphates.
Shuto et al., Tetrahedron Letters, vol. 28, No. 2, 1987, p. 199-202, A Facile One-Step Synthesis of 5'-Phosphatidylnucleosides by an Enzymatic Two-Phase Reaction.
Bosowsky et al., Nucleic Acid Chemistry, Part 3, Editors: L. B. Townsend & R. S. Tipson, 1986, pp. 255-258, Alkyl Esters of 9-(5-O-Phosphone-β-D-Arabinofuranosyl)-Adenine.
Davoll et al., J. Chem. Soc., 1960, pp. 5041-5049, The Synthesis of 9-Glycitylpurines, 3-Glycityl-[1,2,3]-triazolo[d]-pyrimidines, 8-Glycitylpteridines, and 10-Glycitylbenzo[g]pteridines, including and Riboflavin and Riboflavin 2-Imine.
Bencini et al., Analytical Biochemistry, vol. 132, 1983, pp. 254-258 Linear One-Step Assay for the Determination of Orthophosphate.
Sells et al., Proc. Natl. Acad. Sci. U.S.A., vol. 84, Feb. 1987, pp. 1005-1009, Production of hepatitis B virus particles in Hep G2 cells transfected with cloned hepatitis B virus DNA.
E. M. Southern, J. Mol. Biol., vol. 98, 1975, pp. 503-517, Detection of Specific Sequences Among DNA Fragments Separated by Gel Electrophoresis.
Antiviral Research, vol. 9, No. 1/2, Jan./Feb., 1988, ISSN 0166-3542, Elsevier.
Daluge et al., J. Org. Chem., vol. 43, No. 12, 1978, pp. 2311-2320, Synthesis of Carbocyclic Aminonucleosides.
Yeom et al., Antimicrob. Agents Chemotherapy, Feb., 1989, vol. 33, No. 2, pp. 171-175, Pharmacokinetics and Bioavailability of Carbovir, a Carbocyclic Nucleosede Active against Human Immuodeficiency Virus, in Rats.
Vince et al., Biochemical and Biophysical Research Communications, vol. 156, No. 2, Oct. 31, 1988, pp. 1046-1053, Potent and Selective Activity of a New Carbocyclic Nucleoside Analog (Carbovir: NSC 614846) Against Human Immunodeficiency Virus in vitro.
Marquez et al., Nucleosides and Nucleotides, 6(1&2), pp. 239-244 (1987) Synthesis of 2',3'-Dideoxycyclopentenyl Carbocyclic Nucleosides as Potential Drugs for the Treatment of Aids.
Remmel et al., Journal of Chromatography, 489, (1989), pp. 323-331, Liquid Chromatographic Assay of Carbovir, A carbocyclic Nucleoside Active Against Human Immunodeficiency Virus.
Abstract No. 802, MINU, Synergistic Antiviral Combination.
White et al., Biochemical and Biophysical Research, vol. 161, No. 2, Jun. 15, 1989, pp. 393-398, Comparison of the Effect of Carbovir, AZT, and Dideoxynucleoside Triphosphates on the Activity of Human Immunodeficiency Virus Reverse Transcriptase and Selected Human Polymerases.
Chemical Abstracts, vol. 108, No. 21, May 23, 1988.
Chemical Abstracts, vol. 110, No. 7, Feb. 13, 1989.
Chemical Abstracts, vol. 111, No. 5, Jul. 31, 1989.

*Primary Examiner*—Cecilia Shen
*Attorney, Agent, or Firm*—Donald Brown; Lawrence A. Nielsen; Hannah O. Green

[57] ABSTRACT

The present invention relates to 6-substituted purine carbocyclic nucleosides and their use in medical therapy particularly in the treatment of HIV and HBV infections. Also provided are pharmceutical formulations and processes for the preparation of compounds according to the invention.

17 Claims, No Drawings

THERAPEUTIC NUCLEOSIDES

This is a continuation of copending application Ser. No. 07/455,201, filed on Dec. 22, 1989, now U.S. Pat. No. 5,034,394, which is in turn a continuation of Ser. No. 07/371,870, filed on June 26, 1989, now abandoned.

The present invention relates to purine nucleoside analogs containing an unsaturated carbocyclic ring in place of the sugar residue, pharmaceutically acceptable derivatives thereof, and their use in medical therapy, particularly for the treatment of certain viral infections.

AIDS (acquired immunodeficiency syndrome) is an immunosuppressive or immunodestructive disease that predisposes subjects to fatal opportunistic infections. Characteristically, AIDS is associated with a progressive depletion of T-cells, especially the helper-inducer subset bearing the OKT$^4$ surface marker.

Human immunodeficiency virus (HIV) has been reproducibly isolated from patients with AIDS or with the symptoms that frequently precede AIDS. HIV is cytopathic and appears to preferentially infect and destroy T-cells bearing the OKT$^4$ marker, and it is now generally recognized that HIV is the etiological agent of AIDS.

Since the discovery that HIV is the etiological agent of AIDS, numerous proposals have been made for anti-HIV chemotherapeutic agents that may be effective in treating AIDS sufferers. Thus, for example, U.S. Pat. No. 4,724,232 describes 3'-azido-3'-deoxythymidine (which has the approved name zidovudine), its pharmaceutically acceptable derivatives and their use in the treatment of human retrovirus infections including AIDS and associated clinical conditions. Vince et al., *Antiviral Research* 9 (1/2), 120 (1988) describes certain carbocyclic nucleoside analogs and their use against HIV. At the Second International Conference on Antiviral Research, Williamsburg, Va., Apr. 10–14, 1988, (±)-9-(cis-4-(hydroxymethyl)-2-cyclopentenyl)guanine (NSC-614846), also known as carbovir, was disclosed.

Worldwide, hepatitis B virus (HBV) is a viral pathogen of major consequence. It is most common in Asian countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease.

The United States currently contains an estimated pool of 500,000–1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with the HBV virus range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Viral Infections of Humans" (second edition, Ed., Evans, A. S.. (1982) Plenum Publishing Corporation, New York), Chapter 12 describes in detail the etiology of viral hepatitis infections.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck. Recent insights into the mechanism of replication of the hepadnavirus genome indicate the importance of reverse transcription of an RNA intermediate, suggesting that the reverse transcriptase is a logical chemotherapeutic target.

It has now been discovered that certain purine nucleoside analogues containing an unsaturated carbocyclic ring, as referred to below, are useful for the treatment of viral infections, for example, hepatitis B and retroviral infections, especially AIDS.

According to a feature of the present invention, novel compounds of the formula (I) are provided:

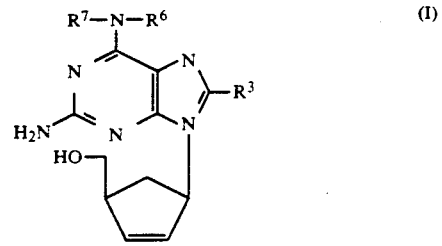

wherein $R^3$ represents hydrogen or $C_{1-6}$ alkyl; $R^6$ represents $C_{3-8}$ cycloalkyl (preferably $C_{3-6}$ cycloalkyl, e.g. cyclopropyl, cyclobutyl or cyclopentyl); and $R^7$ represents a hydrogen atom or branched or straight chain $C_{1-6}$ alkyl (e.g. methyl or ethyl); or a pharmaceutically acceptable derivative thereof.

The most preferred isomers are those in which the hydroxymethyl group is cis to the purine in compounds of formula (I). It is to be understood that the present invention encompasses the individual enantiomers of the compounds of formula (I) as well as wholly or partially racemic mixtures of such enantiomers even though the precise structures as drawn relate to one enantiomer.

Preferred examples of compounds of formula (I) are
a) (−)-cis-4-[2-amino-6-(cyclopropylamino)-9H-purin-9-yl]-2-cyclopentene-1-methanol and racemic or partially resolved mixtures with the (+)-cis enantiomer thereof and
b) (−)-cis-4-[2-amino-6-(cyclopropylmethylamino)-9H-purin-9-yl]-2-cyclopentene-1-methanol and racemic or partially resolved mixtures with the (+)-cis enantiomer thereof.

These compounds are particularly preferred because of the high levels which reach the central nervous system where manifestations of HIV infection are particularly debilitating.

The compounds of formula (I) above and their pharmaceutically acceptable derivatives are hereinafter referred to as the compounds according to the invention.

In one aspect of the invention there are provided the compounds according to the invention for use in medical therapy particularly for the treatment of retroviral infections and hepatitis B viral infections.

Examples of retroviral infections which may be treated or prevented in accordance with the invention include human retroviral infections such as human immunodeficiency virus (HIV), HIV-1, HIV-2 and human T-cell lymphotropic virus (HLTV), e.g. HTLV-I or HTLV-II infections. The compounds according to the invention are especially useful for the treatment of AIDS and related clinical conditions such as AIDS-related complex (ARC), progressive generalised lymphadenopathy (PGL), AIDS-related neurological conditions, such as multiple sclerosis or tropical paraparesis, anti-HIV antibody-positive and HIV-positive conditions and thrombocytopenic purpura. The compounds may also be used in the treatment or prevention of psoriasis.

The compounds of the present invention are particularly applicable for the treatment of asymptomatic infections or diseases in humans caused by or associated with human retroviruses.

In a further aspect of the present invention there is included:
a) A method for the treatment of retroviral infections and hepatitis B infections which comprises treating the subject with a therapeutically effective amount of a compound according to the invention.
b) Use of a compound according to the invention in the manufacture of a medicament for the treatment of any of the above-mentioned infections or conditions.

By "a pharmaceutically acceptable derivative" is meant any pharmaceutically or pharmacologically acceptable salt, ester or salt of such ester, of a compound according to the invention or any other compound which, upon administration to the recipient, is capable of providing (directly or indirectly) a compound according to the invention, or an antivirally active metabolite or residue thereof.

Preferred esters of the compounds of the invention include carboxylic acid esters in which the non-carbonyl moiety of the ester grouping is selected from straight or branched chain alkyl, e.g. n-propyl, t-butyl, n-butyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino acid esters (e.g. L-valyl or L-isoleucyl); and mono-, di- or triphosphate esters. The phosphate esters may be further esterified by, for example, a $C_{1-20}$ alcohol or reactive derivative thereof, or by a 2,3-di($C_{6-24}$)acyl glycerol.

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group.

Any reference to any of the above compounds also includes a reference to a pharmaceutically acceptable salt thereof.

Examples of pharmaceutically acceptable salts of the compounds according to the invention and pharmaceutically acceptable derivatives thereof include base salts, e.g. derived from an appropriate base, such as alkali metal (e.g. sodium), alkaline earth metal (e.g. magnesium) salts, ammonium and $NW_4+$ (wherein W is $C_{1-4}$ alkyl). Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na+$, $NH_4+$, and $NW_4+$ (wherein W is a $C_{1-4}$ alkyl group).

The above compounds according to the invention and their pharmaceutically acceptable derivatives may be employed in combination with other therapeutic agents for the treatment of the above infections or conditions. Examples of such further therapeutic agents include agents that are effective for the treatment of viral infections or associated conditions such as 3'-azido-3'-deoxythymidine (zidovudine), 2',3'-dideoxynucleosides such as 2',3'-dideoxycytidine, 2',3'-dideoxyadenosine and 2',3'-dideoxyinosine, acyclic nucleosides (e.g. acyclovir), interferons such as α-interferon, renal excretion inhibitors such as probenicid, nucleoside transport inhibitors such as dipyridamole, dilazep, mic-, lido- or soluflazine, or hexohendine as well as immunomodulators such as interleukin II and granulocyte macrophage colony stimulating factors, soluble $CD_4$ or genetically engineered derivatives thereof, and phosphonoformic acid. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions (e.g. AIDS) will be in the range of 3.0 to 120 mg per kilogram body weight of the recipient (e.g. a human) per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to 30 μM. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent.

Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous for purine nucleoside derivatives as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The compounds according to the invention may also be presented for use in the form of veterinary formulations, which may be prepared, for example, by methods that are conventional in the art.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The present invention further includes a process for the preparation of a compound according to the invention and pharmaceutically acceptable derivatives thereof which comprises either:

A) treating a compound of formula (II)

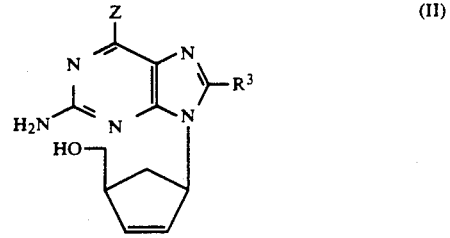

(II)

wherein $R^3$ is as hereinbefore defined and Z represents a precursor group for the $NR^6R^7$ group as defined in formula (I) with an agent or under conditions serving to convert the precursor Z group to the desired $R^2$ group; or B) reacting a compound of formula

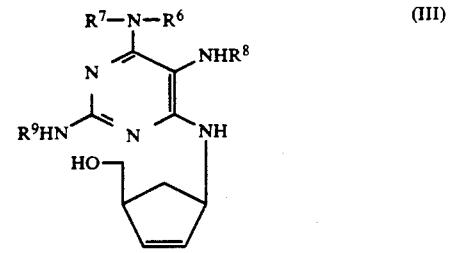

(III)

wherein $R^6$ and $R^7$ are hereinbefore defined, $R^8$ is hydrogen or formyl, and $R^9$ is a $C_{1-6}$ acyl group (e.g., formyl or acetyl) or a pharmaceutically acceptable derivative thereof, with an agent serving to effect formation of the imidazole ring in the desired compound of formula (I); or i) where a compound of formula (I) is formed, converting the said compound to a pharmaceutically acceptable derivative thereof; or ii) where a pharmaceutically acceptable derivative of a compound of formula (I) is formed, converting the said derivative to the parent compound of formula (I) or to a further such derivative.

Process A) above may be carried out in conventional manner, for example, by treatment of a compound of formula (II) in which Z represents a leaving group (e.g. a halo such as a chloro group) with an appropriate amine or amine hydrochloride to introduce a substituted amino group as defined above at reflux or at a temperature greater than 50° C., preferably in the presence of an organic solvent, for example methanol or ethanol.

Process B) may be carried out, for example, by reacting a compound of formula (III) with formic acid or a reactive formic acid derivative (e.g. triethylorthoformate or diethoxymethyl acetate) in a solvent such as a dimethylacetamide or dimethylformamide at an elevated temperature, preferably at 75°-90° C. This reaction is conveniently effected by the addition of slightly more than one equivalent of a strong anhydrous acid, e.g. with 1.1 equivalents of ethanesulfonic acid per equivalent of compound of formula (III), in which case lower temperatures (e.g. 25° C.) are used.

In process A) the starting material of formula (II) may be prepared, for example, by firstly cyclizing a compound of formula (III) above in an analogous manner to that described for process B) above.

Other reagents may be useful for cyclization of compounds of formula (III) to give compounds of formula I where $R^3$ is not hydrogen. For example, triethyl or trimethylorthoacetate with acetic anhydride at 70°-120° C. for several hours gives $R^3=CH_3$ (see H. C. Koppel and R. K. Robins, J. Org. Chem. 1958, 1457).

Alternatively, (1R,4S)-9-(4-hydroxymethyl-2-cyclopentenyl)guanine, prepared, e.g. as described in Australian patent application AU-A-28671/89 (incorporated herein by reference) from aristeromycin, may be converted to compounds of formula (I).

A compound of formula (I) may be converted into a pharmaceutically acceptable ester by reaction with an appropriate esterifying agent, e.g. an acid halide or anhydride. The compound of formula (I), including esters thereof, may be converted into pharmaceutically acceptable salts thereof in conventional manner, for example, by treatment with an appropriate acid. An ester or salt of a compound of formula (I) may be converted into the parent compound, for example by hydrolysis.

The enantiomers of the compounds of formula (I) may be resolved or isolated in conventional manner, e.g. by chromatographic separation of diastereomeric esters prepared by acylation of the hydroxyl on the cyclopentenyl moiety with appropriate optically active carboxylic acid derivatives as, e.g., with naproxen (J. Org. Chem. 1986, 51, 1287). The cyclopentenyl precursors of the compounds of formula (III), may also be resolved by fractional crystallization of salts formed with optically active carboxylic acids (e.g. dibenzoyl-D-tartaric acid). Alternatively, enzymatic resolution may be achieved as in J. Med. Chem. 1987, 30, 746 and J. Med. Chem. 1985, 28, 1385.

The following Examples are intended for illustration only and are not intended to limit the scope of the invention in any way. The term 'active ingredient' as used in the Examples means a compound of formula (I) or a pharmaceutically acceptable derivative thereof.

EXAMPLE 1

(±)-cis-4-[(2-Amino-4-chloro-6-pyrimidinyl)amino-2-cyclopentene-1-methanol cis-4-Acetamidocyclopent-2-enemethyl acetate [U.S. Pat. No. 4,268,672] (14.88 g, 0.073 mol) and barium hydroxide octahydrate (46.19 g, 0.146 mol) were refluxed in water (300 mL) under nitrogen for 18 hours. The resulting solution was neutralized with carbon dioxide. The precipitate was washed with water, then ethanol. The combined filtrate-wash was evaporated to a syrup (11.16 g) which was condensed with 2-amino-4,6-dichloropyrimidine (23.91 g, 0.146 mol) and triethylamine (30.5 mL, 0.219 mol) in refluxing 1-butanol (100 mL) for 1.5 hours. After addition of 1N NaOH (73 mL), the resulting mixture was evaporated to dryness and the residual solid slurried in $CHCl_3$ (200 mL). Unreacted 2-amino-4,6-dichloropyrimidine was filtered off and washed with chloroform (100 mL). The chloroform filtrate-wash was concentrated and chromatographed on a silica gel column. Additional pyrimidine starting material was eluted with 2.5% methanol-chloroform. The title compound was eluted with 3.5% methanol-chloroform as an off-white solid foam (15.90 g, 91%).

$^1$H-NMR: (Me$_2$SO-d$_6$) δ 1.15-1.28 and 2.26-2.41 (2m, 2, $CH_2$); 2.60-2.71 (m, 1, 1'-H); 3.4 (m overlapping $H_2O$, $CH_2OH$); 4.625 (t, J=5.3, 1, $CH_2OH$); 4.95 (hr s, 1, CH—N); 5.67-5.87 (m, 2, CH=CH); 6.38 (br s, 1, $NH_2$); 7.12 (br s, 1, NH); MS (CI) M+1, 241, 243.

Anal Calcd. for $C_{10}H_{13}N_4OCl·0.2H_2O$: C, 48.99; H, 5.55; N, 22.85; Cl, 14.46. Found: C, 49.10; H, 5.57; N, 22.81; Cl, 14.40.

EXAMPLE 2

(±)-cis-4-[[2-Amino-6-chloro-5-[(4-chlorophenyl)azo]-4-pyrimidinyl]amino]-2-cyclopentene-1-methanol (±)-cis-4-[(2-Amino-4-chloro-6-pyrimidinyl)amino]-2-cyclopentene-1-methanol from Example 1 (11.58 g, 48.1 mmol) and sodium acetate trihydrate (97 g) were dissolved in glacial acetic acid (225 mL) and water (225 mL). A cold solution (0°-5° C.) of 4-chlorobenzenediazonium chloride was prepared from 4-chloroaniline (6.74 g, 52.8 mol), concentrated hydrochloric acid (14.7 mL) water (52 mL), and sodium nitrite (4.01 g, 58.2 mmol in 47 mL of water). This cold solution was added dropwise over 5 minutes to the first solution. The resulting yellow precipitate was filtered after 18 hours, washed with water, and extracted with ethanol to give title compound as dark yellow powder (12.56 g, 69%), m.p. 218°-220° C. dec.

$^1$H-NMR: (Me$_2$SO-d$_6$) δ 10.25 (d, 1, NH); 7.69 and 7.54 (both, d, J=8.9, $C_6H_4$) overlapping 7.6 (br, 6, $NH_2$); 5.80-5.95 (m, 2, CH=CH); 5.24 (m, 1, CHN); 4.75 (t, 1, $CH_2OH$); 3.41 (t, 2, $CH_2OH$); 2.75 (m, 1, CH); 2.41 (m, 1, CH); 1.44-1.53 (m, 1, CH).

Anal Calcd. for $C_{16}H_{16}N_6Cl_2O$: C, 50.67; H, 4.25; N, 22.16; Cl, 18.70. Found: C, 50.59; H, 4.29; N, 22.10; Cl, 18.66.

EXAMPLE 3

(±)-cis-4-[(2,5-Diamino-4-chloro-6-pyrimidinyl)-amino]-2-cyclopentene-1-methanol The title compound of Example 2 (11.67 g) was suspended in ethanol (235 mL), glacial acetic acid (30 mL), and water 235 mL). The mixture was heated to reflux under nitrogen. Zinc dust (13.5 g) was added in small portions over 30 minutes during which time the compound dissolved. The reaction was heated an additional 20 minutes, and then the excess zinc was filtered of from the hot solution, and it was washed with ethanol. The filtrates were evaporated, and the residue was purified on a silica gel column eluting with chloroform (1 L) and chloroform:methanol/4:1 (1.8 L). The fractions containing the product were combined, and the solvent was removed under reduced pressure to give the title compound as a red-orange oil (11.2 g, >100% yield). A pure sample was obtained during another small scale reaction to obtain the product as a light yellow solid in a 76% yield.

$^1$H-NMR: (Me$_2$SO-d$_6$) δ 1.29 and 2.39 (m, 2, CH$_2$); 2.69 (t, 1, 1'-H); 3.37 (d, 2, CH$_2$OH); 3.91 (br, 2, NH$_2$); 4.60 (br, 1, CH$_2$OH); 5.02 (m, 1, CHNH); 5.56 (br s, 2, NH$_2$); 5.74 (m, 1, =CH); 5.86 (m, 1, =CH); 6.36 (d, 1, CHNH).

EXAMPLE 4

(±)-cis-4-(2-Amino-6-chloro-9H-purin-9-yl)-2-cyclopentene-1-methanol

The title compound of Example 3 (about 9.7 g) was dissolved in diethoxymethyl acetate (100 g), and refluxed for two days. The solvent was removed under high vacuum at 50° C., and dioxane (40 mL) and 0.5N HCl (60 mL) was added. The reaction was stirred at room temperature for 1.25 hours, and then chilled. The reaction was neutralized to pH 7 with cold 5N sodium hydroxide, and then it was extracted with chloroform:methanol/3:1 several times. The organic layers were dried with magnesium sulphate, filtered, and evaporated. The residue was purified by chromatography on a silica gel column, eluting with 2% MeOH-CHCl$_3$ to give 3.7 8 (46% yield) of the title compound, m.p. 138°–139° C.

$^1$H-NMR: (Me$_2$SO-d$_6$) δ 1.63 and 2.61 (m, 2, CH$_2$); 2.87 (m, 1, 1'-H); 3.44 (d, 2, CH$_2$OH); 5.44 (m, 1, CH-N); 5.89 (m, 1, =CH); 6.14 (m, 1, =CH); 6.82 (br s, 2, NH$_2$); 8.02 (s, 1, 8-H); (CH$_2$OH not seen—under H$_2$O peak). UV: pH 1 λ$_{max}$ 315 (ε 7370); 218 (26200); λ sh 39.5 (5650). pH 7.4 λ$_{max}$ 307 (ε 8000); 245.5 (4600); 223 (26400). MS (EI) 265,267 (m) (CI) 266,268 (m+1).

Anal. Calcd. for C$_{11}$H$_{12}$N$_5$Cl0.2H$_2$O: C, 43.79; H, 5.35; N, 23.21; Cl, 11,75. Found: C, 43.67; H, 5.29; N, 23.05; Cl, 11.70.

EXAMPLE 5

(±)-cis-4-[2-Amino--6-(cyclopropylamino)-9H-purin-9-yl]-2-cyclopentene-1-methanol The title compound of Example 4 (0.50 g) was dissolved in ethanol (40 mL), and cyclopropylamine (0.65 mL, 5 equivalent) was added. The reaction was refluxed under nitrogen for 6 hours. An additional 0.65 mL of cyclopropylamine was added, and the reaction refluxed for an additional 5.5 hours. The solvents were evaporated, and chloroform (25 mL) and saturated sodium bicarbonate solution (5 mL) was added. The aqueous layer was extracted several times with CHCl$_3$ to obtain the crude product. This was purified on a silica gel column eluting with 3% methanol-ethyl acetate to give 0.43 g (80%) of (±-cis-4-[2-amino-6-(cyclopropylamino)-9H-purin-9-yl]-2-cyclopentene-1methanol. This was recrystallized from acetonitrile to give 0.30 g of white powder; m.p. collapses at 93°–130° C.; melts at 165° C.

$^1$H-NMR (Me$_2$SO-d$_6$) δ 0.56 and 0.63 (2m, 4, 2-cyclopropyl CH$_2$); 1.56 and 2.60 (2m, 2, cyclopentenyl CH$_2$); 2.85 (m, 1, 1'-H); 3.02 (m, 1, cyclopropyl CH-NH); 3.43 (m, 2, CH$_2$OH); 4.71 (t, 1, CH$_2$OH); 5.40 (m, 1, 4'-H); 5.77 (s, 2, NH$_2$), overlapping 5.84 (m, 1, =CH$_2$); 6.09 (m, 1, =CH); 7.23 (d, 1, NH—CH); 7.58 (s, 1, purine-8-H); ms (CI) 287 (m+1). UV: pH 1: λ$_{max}$ 296 (ε 14000), 255 (10700); pH 7.0: λ$_{max}$ 284 (15900); 259 (9200); pH 13: λ$_{max}$ 284 (15800), 259 (9100).

Anal. Calcd. for C$_{14}$H$_{18}$N$_6$O.0.25 H$_2$O: C, 57.82; H, 6.41; N, 28.90. Found: C, 57.84; H, 6.45; N, 28.86.

EXAMPLE 6

(±)-cis-4-(2-Amino-6-cyclopentylamino-9H-purin-9-yl)-2-cyclopentene-1-methanol

A solution of (±)-cis-4-(-2-Amino-6-chloro-9H-purin-9-yl)-2-cyclopentene-1-methanol (0.53 g, 2 mmol) from Example 4, triethylamine (2.00 g, 20 mmol), cyclopentylamine (267 mg, 3.1 mmol) and ethanol (10 mL) was stirred at reflux for 9 hours. The solution was allowed to cool to room temperature before the addition of 2 mL of 1.0N NaOH. Concentration of the solution afforded the crude product which was purified by elution from a silica gel column using 5% methanol in chloroform (0.430 g, 68.4%). Crystallization of such a sample from ethanol-acetonitrile gave an off-white powder, m.p. 143°–146° C.

$^1$H-NMR: (Me$_2$SO-d$_6$) δ 7.60 (s, 1H, purine H-8), 7.00 (br, m, 1H, NH) 6.10 and 5.86 (m, 2H, CH=CH), 5.77 (br s, 2H, NH$_2$) 5.39 (m, 1H, NCH cyclopentene), 4.76 (br s, 1H, OH), 4.53 (br m, 1H, NCH), 3.44 (m, 2H, OCH$_2$), 2.87 (m, 1H, CH) 2.62–2.54 (m, 1H, 0.5 CH$_2$ cyclopentene ring), 1.89 (br m, 2H, cyclopentyl CH$_2$), 1.70–1.48 (br, m, 7H, 0.5 CH$_2$ cyclopentene ring, 3CH$_2$).

Anal. Calcd. for C$_{16}$H$_{22}$N$_6$O.0.25 H$_2$O: C, 60.26; H, 7.11; N, 26.35. Found: C, 60.43, 60.37; H, 7.16, 7.17; N, 26.27, 26.25.

EXAMPLE 7

(±)-cis-4-(2-Amino-6-(cyclopropylmethylamino)-9H-purin-9-yl)-2-cyclopentene-1-methanol (±)-cis-4-(2-Amino-6-chloro-9H-purin-9-yl)-2-cyclopentene-1-methanol (0.53 g, 2 mmol) from Example 4, N-methyl-N-cyclopropylamine (Karl Industries, Aurora, Ohio; 0.8477 g, 12 mmol) and methanol (20 mL) were placed in a Parr bomb and heated to 62° C. for 5 hours. The solution was concentrated and then diluted with ethanol before being brought to pH 12 by the addition of 1.0N NaOH. This solution was concentrated and the residue was purified by elution from a silica gel column with 3% methanol-chloroform (0.547 g, 91.2%). Crystallization of such a sample from water-ethanol yielded a white powder, m.p. 130°–131° C.

$^1$H-NMR (Me$_2$SO-d$_6$) δ 7.61 (s, 1H, purine H-8), 6.10 (m, 1H, CH=), 5.84 (m, 1H, CH=), 5.7 (br s, 2H, NH$_2$), 5.40 (m, 1H, CHN), 4.70 (br t, 1H, OH), 3.43 (m, 2H, CH$_2$OH) 3.24 (br s, 4H, CH$_3$, NCH cyclopropyl), 2.85 (m, 1H, CH), 2.66–2.57 and 1.61–1.51 (m, 2, cyclopentenyl CH$_2$), 0.90–0.65 (m, 4H, 2CH$_2$ of cyclopropyl).

Anal. Calcd. $C_{15}H_2ON_6O \cdot 0.5 H_2O$: C, 58.24; H, 6.84; N, 27.16. Found: C, 58.15; H, 6.86; N, 27.14.

EXAMPLE 8

(±)-cis-4-(2-Amino-6-cyclobutylamino-9H-purin-9-yl)-2-cyclopentene-1-methanol

A solution of (±)-cis-4-(2-Amino-6-chloro-9H-purin-9-yl)-2-cyclopentene-1-methanol from Example 4 (0.53 g 2 mmol) and cyclobutylamine (1.387 g, 19.5 mmol) in methanol (15 mL) was heated at 70°-75° C. (oil bath) for 29 hours. After cooling to room temperature, 2 mL of 1.0N NaOH was added. The solution was concentrated and the residue chromatographed on silica gel. Title compound was eluted with 5% methanol-chloroform as colourless foam which solidified to white powder in acetonitrile (454 mg, 75.7%), m.p. 181°-183° C.

$^1$H-NMR: (DMSO-d$_6$) δ 7.59 (s, 1H, purine H.8), 7.38 (br m, 1H, NH), 6.10 (m, 1H 0.5 HC=CH) 5.84 (m overlapping br s, at 5.76, 3H, 0 5 CH=CH, NH$_2$) 5.36 (m, 1H, NCH cyclopentene), 4.73 (t, overlapping br m, J=5.2, 2H, OH, NCH cyclobutane), 3.42 (m, 2H, OCH$_2$), 2.83 (br m, 1H, CH), 2.55 (m overlapping with DMSO, ½ CH$_2$ cyclopentene), 2.20-1.95 (br m, 4H, 2CH$_2$ cyclobutane), 1.58 (m, 3, CH$_2$ cyclobutane, 0.5 CH$_2$ cyclopentene).

Anal Calcd. $C_{15}H_{20}N_6O$: C, 59.98; H, 6.71; N, 27.98. Found: C, 60.05; H, 6.73; N, 27.91.

EXAMPLE 9

(±)-cis-[4-[2-Amino-6-(cyclopropylamino)-9H-purin-9-yl]-2-cyclopenten-1-yl]-methylacetate A solution of (±)-cis-4-(2-amino-6-cyclopropylamino-9H-purin-9-yl)-2-cyclopentene-1-methanol from Example 5 (400 mg, 1.5 mmol), acetic anhydride (228 mg, 2.2 mmol), 4-N,N-dimethylaminopyridine (8.4 mg, 6.9 10$^{-2}$ mmol) and dry N,N-dimethylformamide 112 mL) were stirred at room temperature overnight. The solution was concentrated under high vacuum and the residues were placed on a silica gel column which was eluted with 5% methanol-chloroform, (240 mg, 48.7%). The title compound was diluted in ethanol and foamed under high vacuum.

$^1$H-NMR: (DMSO-d$_6$) δ 7.52 (s, 1H, purine H$_8$), 7.28 (d, J=4.5, 1H, NH), 6.07 and 5.94 (m, 2H, HC=CH) 5.81 (br, 2H, NH$_2$), 5.39 (br m, 1H, NCH), 4.06 (m, 2H, OCH$_2$) 3.02 (br m, 2H, CH, NCH cyclopropane), 2.65 (m, 1H 0.5 CH$_2$ cyclopentene) 1.98 (s, 3H, CH$_3$), 1.56 (m, 1H, 0.5 CH$_2$ cyclopentene), 0.61 (m, 4H, 2CH$_2$ cyclopropane).

Anal. Calcd. $C_{16}H_{20}N_6O_2 \cdot 0.4H_2O \cdot 0.15$ EtOH: C, 57.16; H, 6.39; N, 24.54. Found: C, 56.88, 56.82; H, 6.32, 6.32; N, 24.81, 24.78.

EXAMPLE 10

(±)-cis-[4-(2-Amino-6-(cyclopropylmethylamino)-9H-purin-9-yl]-2-cyclopentene-1-yl]-methyl acetate A solution of (±)-cis-4-(2 amino-6-(cyclopropylmethylamino)-9H-purin-9-yl)-2-cyclopentene-1-methanol from Example 7 (0.30 g, 1 mmol), acetic anhydride (0.204 g, 2 mmol), N,N-dimethylaminopyridine (0.005 g, 0.04 mmol) in N,N-dimethylformamide (10 mL) was stirred at room temperature under nitrogen overnight. H$_2$O (1 mL was added and the solution allowed to stir an additional hour, then concentrated under high vacuum. The residual oil was partitioned between saturated sodium bicarbonate solution (5 mL) and chloroform (3×50 mL). The combined chloroform extracts were dried (MgSO$_4$), solvent evaporated and residue chromatographed on silica gel. Title compound was eluted with 4% methanol-chloroform; foamed from ethanol under high vacuum (0.330 g, 93%).

$^1$H-NMR: (DMSO-d$_6$) δ 7.59 (s, 1, H-8), 6.10 and 5.90 (2m, 2, CH=CH), 5.80 (br s, 2, NH$_2$), 5.40 (br m, 1, CH-N), 4.05 (d, J=6.1, 2, OCH$_2$), 3.30-3.20 (m, overlapping s at 3.23, total 4, CH-N-Me), 3.10 (br m, 1, CH), 2.75-2.60 (m, 1, 0.5 CH$_2$), 1.98 (s, 3, COCH$_3$), 1.65-1.50 (m, 1, 0.5 CH$_2$).

Anal. Calcd. for $C_{17}H_{22}N_6O_2 \cdot 0.45H_2O$ 0.5 EtOH: C, 58.21; H, 6.63; N, 23.82. Found: C, 58.15, 58.09; H, 6.60, 6.61; N, 23.91, 23.83.

EXAMPLE 11

(±)-cis-4-[2-Amino-6(cyclopropylethylamino)-9H-purin-9-yl]-2-cyclopentene-1-methanol A sample of N-cyclopropyl-N-ethylamine was prepared as follows. Cyclopropylamine (18.44 g, 0.323 mole), potassium carbonate (45.6 g, 0.33 mole), and dry diethyl ether (250 mL) were stirred vigorously with cooling (ice bath) while trifluoroacetic anhydride (50 mL, 0.36 mol) was added dropwise over 30 minutes. Ice water (20 mL) was added. The ether layer was separated and dried (MgSO$_4$).

Concentration gave a pale yellow liquid (51.1 g). A portion of this liquid (15.3 g, ca.0.1 mole) was dissolved in dry acetone (250 mL) with ethyl iodide (46.8 g, 0.30 mole) and heated to 70° C. (oil bath). Powdered potassium hydroxide (16.8 g, 0.300 equiv.) was added. Stirring was continued at 70° C. for 30 minutes. Excess ethyl iodide and acetone were removed by evaporation. Water (100 mL) was added to the residue and the resulting solution brought to reflux over 15 minutes (oil bath 110° C.) and maintained at reflux for 5 minutes. The solution was cooled to 25° C., saturated with sodium chloride, and extracted with diethyl ether (3×100 mL). The ether solution was dried (MgSO$_4$) and evaporated to leave pale yellow oil (4.86 g, 57%); $^1$H-NMR (DMSO-d$_6$) δ 7.74 (q, J=6.0, 2, NCH$_2$CH$_3$), 2.2-2.08 (m, 1, CHN), 1.97 (br s, NH+H$_2$O), 1.19 (t, J=6.0, 3, NCH$_2$CH$_3$), 1.9-1.3 (m, 4, 2CH$_2$). Such a sample of N-cyclopropyl-N-ethylamine (1.26 g) was heated with (±)-(cis)-4-(2-amino-6-chloro-9H-purin-9-yl)-2-cyclopentene-1-methanol from Example 4 (544 mg, 2.00 mmol) in methanol (16 mL) in a Parr bomb at 75° C. for 11.5 hours. Sodium hydroxide (1N, 1.5 mL) was added and the solution evaporated to dryness. The residue was chromatographed on silica gel. Title compound was eluted with 4% methanol-chloroform as pale yellow-glass which crystallized from acetonitrile; 298 mg (47%); m.p. 152°-154° C.

$^1$H-NMR: (DMSO-d$_6$) δ 7.64 (s, 1H, purine H-8), 6.11 and 5.88 (m, 2, HC=CH), 5.80 (br s, 2, NH$_2$), 5.42 (m, 1, NCH cyclopentene) 4.75 (t, J=4.8, 1, OH), 3.94 (m, 2, NCH$_2$), 3.45 (m, 2, OCH$_2$), 3.05 (m, 1, NCH cyclopropane), 2.87 (br m, 1, CH), 2.60 (m, overlapping with DMSO, 0.5 CH$_2$ cyclopentene), 1.56 (m, 1, 0.5 CH$_2$ cyclopentene), 1.10 (t, J=6.9, CH$_3$), 0.85 and 0.65 (m, 4, 2CH$_2$).

Anal. Calcd. for $C_{16}H_{22}N_6O$: C, 61.13; H, 7.05; N, 26.73. Found: C, 61.06; H, 7.07; N, 26.66.

EXAMPLE 12

(±)-cis-[4-[2-Amino-6-(cyclopropylamino)-9H-purin-9-yl]-2-cyclopenten-1-yl]-methyl L-valinate trifluoroacetate N-Butyloxycarbonyl-L-valine 11.200 g, 5.19 mmol) and N,N-dicyclohexyl-carbodiimide (0.562 g, 2.73 mmol) were stirred in dry methylene chloride (46 mL) for 40 minutes. The mixture was filtered, the precipitate washed with methylene chloride (8 mL), and the filtrate-wash evaporated to dryness. This residual white solid (anhydride) was added in two portions to (±)-cis-4-(2-Amino-6-(cyclopropylamino)-9H-purin--9-yl)-2-cyclopentene-1-methanol from Example 5 (572 mg, 2.00 mmol), dry N,N-dimethylformamide (19 mL) and 4-N,N-dimethylaminopyridine (20 mg, 0.16 mmol). The reaction was stirred at 25° C. under nitrogen for 69 hours, before the addition of water (0.3 mL). The solution was evaporated to dryness and the residue partitioned between chloroform and $NaHCO_3$ (2.5 mmol) in $H_2O$. The aqueous layer was extracted with chloroform and the combined organic layers were dried ($MgSO_4$), filtered. Elution with 4% methanol-chloroform gave the N-butyloxy-carbonyl-blocked derivative of the title compound as white foam (520 mg).

$^1$H-NMR: ($Me_2SO$-$d_6$) δ 7.62 (s, 1, purine H-8), 7.30 (d, J=3.9, 1, NH cyclopropylamine), 7.16 (d, J=7.9, 1, CHN), 6.08 and 5.95 (m, 2, HC=CH), 5.83 (br s, 2, $NH_2$), 5.42 (br m, 1, NCH), 4.13 (d, J=6.3, 2, $OCH_2$), 3.82 (t, J=7.4, 1, NCH of valyl), 3.08 (br m, 2, CH cyclopentene, CH cyclopropane) 2.69 (m, 1, 0.5 $CH_2$ cyclopentene), 1.97 (m, 1, $CHMe_2$), 1.60 (m, 1, 0.5 $CH_2$ cyclopentene), 1.37 (s, 9, $\overline{C(CH)_3}$), 0.88–0.79 (overlapping d, 6, $CH(\underline{CH_3})_2$), 0.64 and $\overline{0.59}$ (m, 4, $2CH_2$ cyclopropane). This derivative (510 mg) was dissolved in trifluoracetic acid:methylene chloride/1:3 (~25 mL) and the solution stirred at 25° C. for 30 minutes. Evaporation left the title compound as a yellow foam (745 mg).

$^1$H-NMR: (DMSO-$d_6$) δ 9.85 (br m, 1,NH), 8.37 (br m, 3, $NH_3+$), 8.01 (br s, 1, purine H-8), 7.57 (br s, 2, $NH_2$), 6.17 and 6.02 (m, 2, HC=CH), 5.48 (m, 1, NCH cyclopentene), 4.26 (m, overlapping br solvent, $OCH_2$), 3.94 (br m, overlapping solvent, valyl CH), 3.17 (m, 1, CH), 2.9–2.68 (br m, 2, cyclopropyl CHN, 0.5 $CH_2$ cyclopentene), 2.14 (m, 1, $CHMe_2$), 1.66 (m, 1, 0.5 $CH_2$ cyclopentene), 0.94 (m, 8, $CH\underline{Me_2}$, $CH_2$ cyclopropane), 0.78 (m, 2, cyclopropyl $CH_2$).

Anal. Calcd. for $C_{19}H_{27}N_7O_2 \cdot 0.8\ H_2O \cdot 3.8\ CF_3CO_2H$: C, 38.35; H, 3.92; N, 11.77. Found: C, 38.25; H, 3.79; N, 11.80.

EXAMPLE 13

(±)-cis-4-[2-Amino-6(cyclobutylmethylamino)-9H-purin-9-yl]-2-cyclopentene-1-methanol A sample of N-cyclobutyl-N-methylamine was prepared as follows. Cyclobutylamine (5.00 g, 68.9 mmol) and potassium carbonate (13.3 g, 96.5 mmol) were vigorously stirred in dry diethyl ether (250 mL) under nitrogen in an ice bath while trifluoroacetic anhydride (10.7 mL) was added dropwise over 20 minutes. Ice water (20 mL) was added. The ether layer was separated, dried ($MgSO_4$), and concentrated to a colourless liquid (11.50 g). This liquid was dissolved in dry acetone (170 mL) with methyl iodide (40 g, 0.28 mole) and heated to 40° C. Powdered potassium hydroxide (16 g, 0.28 equiv.) was added. Stirring at 40° C. was continued for 45 minutes. The excess methyl iodide and acetone were removed by evaporation and water (75 mL) was added to the residual liquid and solids. The resulting solution was brought to reflux over 15 minutes (oil bath 110° C.) and maintained at reflux for 5 minutes. The solution was cooled to 25° C., saturated with sodium chloride, and extracted with diethyl ether (3×50 mL). The ether solution was dried ($MgSO_4$) and evaporated to leave colourless oil (3.72 g, 64%). $^1$H-NMR (CDCl$_3$) δ3.25–3.15 (m, 1, CHN), 2.34 (s, 3, $NCH_3$), 2.27–2.03 (m, 2, 2CH), 1.8–1.6 (m, 4, $CH_2$ and 2CH). Such a sample of N-cyclobutyl-N-methylamine (510 mg, 6.0 mmol) was heated with (±)-(cis)-4-(2-amino-6-chloro-9H--purin-9-yl)-2-cyclopentene-1-methanol from Example 4 (544 mg, 2.00 mmol) in methanol (16 mL) in a Parr bomb at 65° C. for 5.5 hours. Sodium hydroxide (1N, 2 mL) was added and the solution evaporated to dryness. The residue was chromatographed on silica gel. Title compound was eluted with methanol-chloroform as a pale yellow solid foam, from acetonitrile; 528 mg, 84%.

$^1$H-NMR: (DMSO-$d_6$) δ 7.62 (s, 1, purine H-8), 6.15–6.07 (m, 1, =CH), 6.0–5.7 (m, 4, CH=CH, $NH_2$, and cyclobutyl CHN), 5.5–5.3 (m, 1, CHN), 4.77 (t, J=5.3, 1, OH), 3.42 (m, 2, $\underline{CH_2}OH$), 3.27 (s, overlapped by $H_2O$, N—$CH_3$), 2.85 (m, 1, H-1'), 2.7–2.5 (m, 1, 0.5 cyclopentyl $CH_2$), 2.4–2.0 (m 4, 2 cyclobutyl $CH_2$), 1.7–1.4 (m, 3, 0.5 cyclopentyl $CH_2$ and cyclobutyl $CH_2$).

Anal. Calcd. for $C_{16}H_{22}N_6 \cdot 0.03H_2O \cdot 0.05CH_3CH$: C, 60.08; H, 7.12; N, 26.33. Found: C, 60.02, 59.97; H, 7.10, 7.13; N, 26.30, 26.26.

EXAMPLE 14

(±)-cis-[4-[2-Amino-6-(cyclopropylmethylamino)-9H-purin-9yl-2-cyclopentene-1-yl)-methyl-L-valinate trifluoroacetate N-Butyloxycarbonyl-L-valine (1.09 g, 5.0 mmol) and N,N-dicyclohexylcarbodiimide (0.515 g, 2.5 mmol) were stirred in dry methylenechloride (15 mL) for 1 hour. The mixture was filtered, the precipitate was washed with methylene chloride (10 mL), and the filtrate-wash was evaporated to dryness. To this was added (±)-cis-4-(2-amino-6-(cyclopropylmethylamino)-9-purin-9-yl]-2-cyclopentene-1-methanol from Example 7 (0.600 g, 2 mmol), dry N,N-dimethylformamide (15 mL) and 4-N,N-dimethylaminopyridine (5 mg, 0.04 mmol). The reaction was stirred at room temperature under nitrogen for 16 hours. $H_{20}$ (1 mL) was added and the solution was concentrated under vacuum. The residual oil was partitioned between 0.1N NaOH (2 mL) and chloroform (3×50 mL). The combined chloroform extracts were dried ($MgSO_4$), solvent evaporated and the residue chromatographed on silica gel. Elution with 5% methanol-chloroform gave the N-butyloxycarbonyl-blocked derivative of the title compound as a white solid (0.750 g, 75%).

$^1$H-NMR: (DMSO-$d_6$) δ 7.62 (s, 1, H-8), 7.15 (d, J=8.2, 1, NH), 6.10 and 5.90 (2m, 2, CH=CH), 5.79 (br s, 2, $NH_2$), 5.40 (br m, 1, CH—N), 4.10 (d, J=6.4, 2, $CH_2$—O), 3.80 (m, 1 valyl CH—N), 3.30–3.15 (m, overlapping s at 3.23, total 4, CH—N—Me), 3.10–3.0 (br m, 1, CH), 2.75–2.55 (m, 1, 0.5 $CH_2$), 2.05–1.85 (m, 1, $CHMe_2$), 1.70–1.50 (m, 1, 0.5 $CH_2$), 1.34 (m, 9, $CMe_3$), 0.90–0.60 (m, 10, CH-$Me_2$ and cyclopropyl $CH_2$). Such a sample (0.74 g, 1.5 mmol) was dissolved in trifluoroacetic acid:methylene chloride/1:3 (25 mL) and the solution stirred at 25° C. under nitrogen for 30 minutes.

Evaporation left the title compound as a yellow foam (0.957 g, 87%), $^1$H-NMR: (DMSO-d$_6$) δ 8.38 (br s, 3, NH$_3$+), 8.0 (s, 1, H-8), 7.80-7.10 (br m, 2, NH$_2$), 6.18 and 6.0 (2m, 2, CH=CH), 5.48 (m, 1, CH—N), 4.26 (br d, J=6.5, overlapped by H$_2$O), CH$_2$-O) 3.93 (br m, 1, CH—N valyl), 3.55 (br s, 3, N-Me), 3.20-3.10 (br m, 2, CH and cyclopropyl CH—N), 2.79-2.69 (m, 1, 0.5 CH$_2$), 2.20-2.05 (m, 1, CHMe$_2$), 1.67-1.60 (m, 1, 0.5 CH$_2$), 1.10-0.90 (m, 10, 2 CH$_3$ and 2 cyclopropyl CH$_2$).

Anal. Calcd. for C$_{20}$H$_{29}$N$_7$O$_2$.1.0H$_2$O.0.4EtOH.2.60CF$_3$CO$_2$H: C, 42.64; H, 4.95; N, 13.39. Found: C, 42.63; H, 4.91; N, 13.42.

EXAMPLE 15

(±)-cis-4-[2-Amino-6-(cyclooctylamino)-9H-purin-9yl]-2-cyclopentene-1-methanol (±)-cis-4-(2-Amino-6-chloro-9H-purin-9-yl)-2-cyclopentene-1-methanol (0.549 g, 2 mmol), cyclooctylamine (0.762 g, 6 mmol) and ethanol (15 mL) were stirred at reflux under nitrogen for 20 hours 1N NaOH (2 mL) was added and solvent was evaporated. The residual oil was chromatographed on silica gel. Title compound was eluted with 5% methanol-chloroform as white powder after crystallization from acetonitrile-methanol (0.623 g, 87%); m.p. 171°-173° C.

$^1$H-NMR: (DMSO-d$_6$) δ7.60 (s, 1H, H-8), 6.90 (m, 1, NH), 6.10 and 5.85 (2 m, 2, CH=CH), 5.75 (br s, 2, NH$_2$), 5.40 (m, 1, CHN), 4.76 (t, J=5.1, 1, OH), 4.30 (br m, 1, CH-N), 3.45 (m, 2, CH$_2$-O), 2.85 (br m, 1, CH), 2.70-2.55 (m, 1, ½CH$_2$), 1.85-1.40 (br m, 14, 7 CH$_2$ and ½CH$_2$).

Anal. Calcd. C$_{19}$H$_{28}$N$_6$O: C, 64.02; H, 7.92; N, 23.58. Found: C, 64.11; H, 7.97; N, 23.51.

EXAMPLE 16

(±)-cis-4-[2-Amino-6-(cyclopropylamino)(-8-methyl-9H-purin-9-yl]-2-cyclopentene-1-methanol (±)-cis-4-[(2,5-Diamino-4-chloro-6-pyrimidinyl)amino]-2-cyclopentene-1-methanol prepared as in Example 3 (1.12 g, 4.38 mmol) was stirred in N,N-dimethylformamide (5 mL) with trimethylorthoacetate (30 mL) and ethane sulfonic acid (0.66 g, 5.7 mmol) at 70° C. for 3 days. The resulting solution was evaporated to a yellow syrup. Acetic anhydride (20 mL) was added and this solution was refluxed for 2.5 hours. The resulting dark solution was evaporated to a syrup, which was dissolved in 1N hydrochloric acid (50 mL). After 24 hours, the pH was adjusted to 6 with sodium hydroxide and most of the water evaporated. Crude product was extracted into 20% isopropyl alcohol-chloroform. This solution was dried (MgSO$_4$) and solvent evaporated to leave (±)-cis-4-(2-amino-6-chloro-8-methyl- 9H-purin-9-yl)-2-cyclopentene-1-methanol as a pale yellow glass (0.30 g); structure confirmed by $^1$H-NMR. This sample was dissolved in methanol (10 mL) and stirred in a Parr bomb with cyclopropylamine (1 mL) at 70° C. for 12 hours. Evaporation and chromatography on silica gel gave title compound, eluted as a cream-colored solid foam (136 mg) with 5% methanol-chloroform.

$^1$H-NMR: (DMSO-d6) δ 7.13 (d, J=4.6, 1, NH), 6.02 and 5.84 (both m, 2, CH=CH), 5.68-5.56 (m, 3, NH$_2$ and CH-N), 4.85 (t, 1, CH$_2$OH), 3.53 (m, 2, CH$_2$OH), 3.02 (m, 1, CH-N of cyclopropyl), 2.88 (m, 1, CH), 2.5 (m, overlapping solvent, 0.5 cyclopentyl CH$_2$), 1.72 (m, 1, 0.5 cyclopentyl CH$_2$), 0.7-0.5 (m, 4, 2 cyclopropyl CH$_2$).

Anal. Calcd. for C$_{15}$H$_{20}$N$_6$O.0.25CH$_3$OH.0.65H$_2$O: C, 57.23; H, 7.02; N, 26.26. Found: C, 57.55; H, 6.99; N, 25.95.

EXAMPLE 17

(−)-cis-4-[2-Amino-6-(cyclopropylamino)-9H-purin-9-yl-2-cyclopentene-1-methanol

The title compound of Example 5 (0.600 g, 2.00 mmol) was dissolved in 1,3-dimethyl-3,4,5,6-tetrahydro-2-(1H)-pyrimidinone (Aldrich, 12 mL). Phosphoryl chloride (0.76 mL, 8.0 mmol) was added to the stirred, cooled (−10° C.) solution. After 3 minutes, cold water (100 mL) was added and the resulting solution neutralized with 3M ammonium hydroxide. The neutralized solution was diluted to 1 liter with water and applied to a 2.5×20 cm column of DEAE Sephadex A25 (Pharmacia) which had been preequilibrated with 50 mM ammonium bicarbonate. The column was first washed with 4 liters of 50 mM ammonium bicarbonate. The 5'-monophosphate of (±)-cis-4-[2-amino-6-(cyclopropylamino)-9H-purin-9-yl]-2-cyclopentene-1-methanol was then eluted with a 2-liter gradient of 50 to 300 mM ammonium bicarbonate. The fractions containing nucleotide were evaporated to a white powder to remove ammonium bicarbonate; 71% calculated by UV absorbance; one peak by HPLC (see below). Snake venom 5'-nucleotidase (EC 3.1.3.5) from *Crotalus atrox* (1000 IU, Sigma) was added to 1.4 mmoles of nucleotide dissolved in water (20 mL). The solution was incubated at 37° C. for 22 hours, at which time additional enzyme (1000 IU) was added. Incubation was continued for another 3 days. HPLC analysis (0.4×10 cm Whatman Partisil 10 strong anion exchange column; elution with a gradient of 20 mM to 1M ammonium phosphate, pH 5.5, containing 5% methanol; UV detection at 284 nM) at this point showed that 50% of the starting nucleotide had been dephosphorylated bo bhe nucleoside. This mixture was again applied to a DEAE Sephadex column as described above. Elution with 4 liters of 50 mM ammonium bicarbonate gave fractions containing the title compound. Evaporation of the water left white powder. This material was further purified by chromatography on silica gel with MeOH:CHCl$_3$/1:9 to give colorless glass. The glass was solidified in acetonitrile to give (−)-cis-4-[2-amino-6-(cyclopropylamino)-9H-purin-9-yl]-2-cyclopentene-1-methanol as white gummy solid which was dried to a solid foam at 0.5 mm Hg at 68° C. (260 mg, 86% from racemate); $^1$H-NMR in DMSO-d$_6$ and mass spectrum identical with those of the racemate (title compound of Example 5); [α]$^{20}_D$ −59.7°, [α]$^{20}_{436}$ −127.8°, [α]$^{20}_{365}$ −218.1°, (c=0.15, methanol).

Anal. Calcd. for C$_{14}$H$_{18}$N$_6$O.0.8H$_2$O: C,55.91; H, 6.57; N, 27.94. Found: C, 56.05; H, 6.65; N, 27.88.

Continued elution of such a Sephadex column with a 2-liter gradient of 50 to 300 mM ammonium bicarbonate gave the 5'-monophosphate (see Example 19) which was stable to 5'-nucleotidase.

EXAMPLE 18

5'-Monophosphate of (−)-cis-4-[2-Amino-6-(cyclopropylamino)-9H-purin-9-yl]-2-cyclopentene-1-methanol The title compound of Example 17 (0.35 g, 1.2 mmol) was dissolved in 1,3-dimethyl-3,4,5,6-tetrahydro-2-(1H)-pyrimidinone (Aldrich, 5 mL). Phosphoryl chloride (Aldrich, 0.43 mL, 4.6 mmol) was added to the stirred, cooled (−10° C.) solution. After 3 minutes, cold water (20 mL) was added and the resulting solution neutralized with 3M ammonium hydroxide. Ion exchange chromatography as in Example 17 gave the nucleotide as the diammonium salt after evaporation of water, white powder (95% yield, quantitated by UV); HPLC analysis as in Example 17 shows one peak; UV $\lambda_{max}$ nM (0.1 M HCl): 254, 297; (pH 7 phosphate buffer):259, 284; (0.1 M NaOH):259, 284. The base/phosphate ratio was 1.0/1.3 as determined by the method of B. Ames (*Methods in Enzymology* 8:115, 1966). $[\alpha]^{20}_D$ −69.9°, $[\alpha]^{20}_{578}$ −73.0°, $[\alpha]^{20}_{546}$ −84.0° (c=0.52, MeOH: H$_2$O/4:1).

EXAMPLE 19

5'-Monophosphate of (+)-cis-4-[2-Amino-6-(cyclopropylamino)-9H-purin-9-yl]-2-cyclopentene-1-methanol Elution of the DEAE Sephadex column described in Example 17 after 5'-nucleotidase incubation with a 2-liter gradient of 50 to 300 mM ammonium bicarbonate gave nucleotide-containing fractions which, after evaporation of water, gave title compound as the diammonium salt; white powder (56% from title compound of Example 5); HPLC analysis as in Example 17 shows one peak; UV $\lambda_{max}$ nM (0.1M HCl): 254, 297; (pH 7 phosphate buffer): 259, 284; (0.1M NaOH): 259, 284. The base/phosphate ratio was 1.0/0.98. $[\alpha]^{20}_D$ +62.0°, $[\alpha]^{20}_{578}$ +65.2°, $[\alpha]^{20}_{546}$ +75.0°, (C=0.54, MeOH:-H$_2$O/4.1).

EXAMPLE 20

(+)-cis-4-[2-Amino-6-(cyclopropylamino)-9H-purin-9-yl]-2-cyclopentene-1-methanol The title compound of Example 19 (0.67 mmole) was dissolved in water (20 mL) and alkaline phosphatase (EC 3.1.3.1) from calf intestine (3000 IU, Boehringer Mannheim) was added. The solution was incubated at 37° C. for 19 hours, at which point HPLC analysis as in Example 17 showed that all of the nucleotide had been dephosphorylated. The solution was evaporated to dryness and the residual solids extracted with refluxing ethanol (100 mL). The ethanol-soluble material was adsorbed on silica gel and applied to a silica gel column. Title compound was eluted with methanol:-chloroform/1:9. Evaporation of an acetonitrile-ethanol solution gave white solid foam (164 mg, 79%); $^1$H-NMR in DMSO-d$_6$ and mass spectrum identical with those of the racemate (title compound of Example 5); $[\alpha]^{20}_D$ +58.7°, $[\alpha]^{20}_{436}$ +126.2°, $[\alpha]^{20}_{365}$ +217.5°, (c=0.10, methanol).

Anal. Calcd. for C$_{14}$H$_{18}$N$_6$O.0.60 H$_2$O.0.15EtOH: C, 56.49; H, 6.66; N, 27.64. Found: C, 56.60; H, 6.63; N, 27.55.

EXAMPLE 21

(−)-cis-4-[2-Amino-6-(cyclopropylmethylamino)-9H-purin-9-yl]-2-cyclopentene-1-methanol The title compound of Example 7, (2.00 g, 6.50 mmol) was dissolved in 1,3-dimethyl-3,4,5,6-tetrahydro-2(1H)-pyrimidinone (Aldrich, 20 mL). Phosphoryl chloride (2.28 mL, 24.0 mmol) was added to the stirred, cooled (−10° C.) solution. After 3 minutes, cold water (80 mL) was added. The solution was extracted with chloroform (3×80 mL). The aqueous layer was diluted with ethanol (400 mL) and the pH adjusted to 6 with saturated aqueous NaOH. The precipitated inorganic salts were filtered off. The filtrate was further diluted with ethanol to a volume of 1 liter and the pH adjusted to 8 with additional NaOH. The resulting precipitate was filtered and dried to give the 5'-monophosphate of (±)-cis-4-[2-amino-6-(cyclopropylmethylamino)-9H-purin-9-yl]-2-cyclopentene-1-methanol as white powder (4.0 mmoles, 62% quantitated by UV absorbance); HPLC analysis as in Example 17 shows one peak. This racemic 5'-monophosphate was dissolved in water (200 mL) and snake venom 5'-nucleotidase (EC 3.1.3.5) from *Crotalus atrox* (5,000 IU, Sigma) was added. After incubation at 37° C. for 10 days, HPLC analysis as in Example 17 showed that 50% of the starting nucleotide had been dephosphorylated to the nucleoside. These were separated on a 5×14 cm column of DEAE Sephadex A25 (Pharmacia) which had been preequilibrated with 50 mM ammonium bicarbonate. Title compound was eluted with 2 liters of 50 mM ammonium bicarbonate. Evaporation of water gave white powder which was dissolved in methanol, adsorbed on silica gel, and applied to a silica gel column. Title compound was eluted with methanol:chloroform/1:9 as a colorless glass. An acetonitrile solution was evaporated to give white solid foam, dried at 0.3 mm Hg over P$_2$O$_5$; 649 mg (72% from racemate); $^1$H-NMR in DMSO-d$_6$ and mass spectrum identical with those of the racemate (title compound of Example 7); $[\alpha]^{20}_D$ −48.0°, $[60]^{20}_{436}$ −97.1°, $[\alpha]^{20}_{365}$ −149° (c=0.14, methanol).

Anal. Calcd. for C$_{15}$H$_{20}$N$_6$O.0.10 CH$_3$CN: C, 59.96; H, 6.72; N, 28.06. Found: C, 59.93; H, 6.76; N, 28.03.

Continued elution of the Sephadex column with 2 liters of 100 mM ammonium bicarbonate and then with 2 liters of 200 mM ammonium bicarbonate gave 5'-monophosphate (see Example 22) which was stable to 5'-nucleotidase.

EXAMPLE 22

(+)-cis-4-[2-Amino-6-(cyclopropylmethylamino)-9H-purin-9-yl]-2-cyclopentene-1-methanol The fractions containing nucleotide eluted from the Sephadex column of Example 21 were combined and alkaline phosphatase (EC 3.1.3.1) from calf intestine (4800 IU, Boehringer Mannheim) was added. The solution was incubated at 25° C. for 18 hours, at which point HPLC analysis showed that all of the nucleotide has been dephosphorylated. The solution was evaporated to dryness and the residual solids extracted with refluxing ethanol (100 mL). The ethanol-soluble material was adsorbed on silica gel and applied to a silica gel column. Title compound was eluted with methanol:-chloroform/1:9 as a colorless glass. An acetonitrile solution was evaporated to give white solid foam, dried at 0.3 mm Hg over P$_2$O$_5$; 659 mg (73% from racemate); $^1$H-NMR in DMSO-d$_6$ and mass spectrum identical with those of the racemate (title compound of Example 7); $[\alpha]^{20}_D$ +47.0°, $[\alpha]^{20}_{436}$ +93.0°, $[\alpha]^{20}_{365}$ +141.3° (c=0.11, methanol).

Anal. Calcd. for C$_{15}$H$_{20}$N$_6$O.0.1 CH$_3$CN: C, 59.95; H, 6.72; N, 28.06. Found: C, 59.92; H, 6.80; N, 27.96.

EXAMPLE 23

(1S,1R)-4Amino-2-cyclopentene-1-methanol dibenzoyl-D-tartrate (+)-cis-4-Acetamidocyclopen-2-enemethyl acetate was hydrolyzed with barium hydroxide as in Example 1. The resulting syrup (acetic acid salt of (±)-4-amino-2-cyclopentene-1-methanol) was converted to free amine by stirring with an excess of Amberlite IRA-400 (OH⁻) resin in water. The resin was filtered off, washed with water, and the filtrate-wash evaporated to a pale yellow syrup which was dried by evaporation of portions of ethanol. Such a sample of amine (2.26 g, 20.0 mmol) and dibenzoyl-D-tartaric acid (Aldrich, 3.62 g, 10.0 mmol as 99%) were dissolved in hot absolute ethanol (35 mL). Refluxing acetonitrile (ca. 150 mL) was added to the cloud point and the solution was allowed to cool slowly to room temperature. The white needles which formed were recrystallized three times from the same solvent combination to give title compound as white plates (1.07 g, 37%); m.p. 160°–162°; $[\alpha]^{20}_D$ +66.9°, $[\alpha]^{20}_{436}$ +165°, $[\alpha]^{20}_{365}$ +325° (c=0.28, methanol). X-ray crystallography of this salt allowed the absolute configuration of the cation to be fixed by the known configuration of the D-dibenzoyl tartaric acid dianion. This salt crystallized in the space group C2 with one $C_6H_{12}NO$ cation and one-half $C_{18}H_{14}O_8$ dianion as the asymmetric unit.

Anal. Calcd. for $C_6H_{11}NO·\frac{1}{2}(C_{18}H_{14}O_8)$: C, 61.63; H, 6.21; N, 4.79. Found: C, 61.56; H, 6.24; N, 4.74.

EXAMPLE 24

(1R, 4S)-4-Amino-2-cyclopentene-1-methanol dibenzoyl-L-tartrate

This salt was formed and crystallized exactly as in Example 23, except that dibenzoyl-L-tartaric acid was used. Three crystallizations from ethanol-acetonitrile gave title compound as white plates (1.00 g, 34%); m.p. 160°–162°; $[\alpha]^{20}_D$ −68.2°, $[\alpha]^{20}_{436}$ −169°, $[\alpha]^{20}_{365}$ −333°, (c=0.24, methanol).

Anal. Calcd. for $C_6H_{11}N_{O·\frac{1}{2}}(C_{18}H_{14}O_8)$: C, 61.63; H, 6.21; N, 4.79. Found: C, 61.59; H, 6.21; N, 4.76.

EXAMPLE 25

(±)-cis-N-[4-chloro-5-formamido-6-[[4-(hydroxymethyl)-2-cyclopentene-1-yl]amino]-2-pyrimidinyl]acetamide N-(5-Amino-4,6-dichloropyrimidin-2-yl)acetamide (J. Org. Chem. 1975, 40, 3141) was formylated by addition of 96% formic acid (20 mL) to a solution of (0.75 g, 3.4 mmoles) dissolved in acetic anhydride (20 mL). The resulting solution was stirred at 25° C. for one hour and then evaporated to give N-(4,6-dichloro-5-formamido-2-pyrimidinyl)acetamide as tan powder (0.77 g, 91%); structure confirmed by ¹H-NMR and mass spectrum. This tan powder (840 mg, 3.37 mmol), (±)-cis-4-amino-2-cyclopentene-1-methanol (940 mg, 8.2 mmol), and triethylamine (0.80 g, 8.0 mmol) were warmed in ethanol (50 mL) in an oil bath (70°–80° C.) under nitrogen for 50 minutes and evaporated to a dark oil which was chromatographed on silica gel. Title compound was eluted with 5% methanol-chloroform as a peach-colored solid foam (840 mg). Crystallization from methanol gave white granules (575 mg, 52%); m.p. 189°–193°; ¹H-NMR (DMSO-d₆) δ 10.23 (br, 1.0, NHAc), 9.3 (br, 1.0, NHCHO), 8.15 and 7.90 (both s, total 1.0, HC=O from two conformers, peaks coalesce at 60° C.), 7.42 and 7.22 (both d, J=8.3, total 1.0, CH—NH from two conformers, peaks coalesce at 60° C.), 5.9 and 5.7 (both m, 2.0, CH=CH), 5.05 (m, 1, CH—N), 4.73 (m, 1, OH) 3.39 (m, 2, CH₂OH), 2.72 (m, 1, CH), 2.40 (m, 1, ½ CH₂), 1.36 (m, 1, ½ CH₂).

Anal. Calcd. for $C_{13}H_{16}N_5O_3Cl$: C, 47.93; H, 4.95; N, 21.50; Cl, 10.88. Found: C, 47.99; H, 4.96; N, 21.42; Cl, 10.96.

EXAMPLE 26

(±)-cis-4-[2-Amino-6-(cyclopropylamino)-9H-purin-9-yl]-2-cyclopentene-1-methanol The title compound of Example 25 (0.91 g, 2.79 mmol) was dissolved in dry DMF (1 mL). Triethylorthoformate (10 mL) and ethane sulfonic acid (0.29 mL, 3.4 mmol) were added and the solution heated at 65° C. for 24 hours. The solution was evaporated to a syrup. The syrup was dissolved in 1N HCl (15 mL) and stirred for three hours. The pH was adjusted to 7 with 5N sodium hydroxide and the resulting mixture (oil formed) was extracted with i-propanol:chloroform/1:3 (3×100 mL). The combined organic layers were dried (MgSO₄) and evaporated to a red glass (0.93 g). A solution of this glass in methanol (20 mL) was heated with cyclopropylamine (2 mL) in a Parr bomb at 70° C. for 18 hours. The resulting solution was evaporated to a dark glass which was adsorbed on silica gel. Elution with 7% methanol-ethylacetate gave title compound (148 mg, 19%) as white powder, after trituration with acetonitrile; ¹H-NMR (DMSO-d₆) identical with that of the title compound of Example 5.

In the same manner, the product of Example 23 is converted to the products of Example 17 or Example 21 (using N-methyl-N-cyclopropylamine in the last step).

EXAMPLE 27

(+)-(1R,4S)-cis-N-[4-Chloro-5-formamido-6-{[4-(hydroxymethyl)-2-cyclopentene-1-yl]amino}-2-pyrimidinyl]acetamide (1S,4R)-4-Amino-2-cyclopentene-1-methanol dibenzoyl-D tartrate prepared as in Example 23 (2.76 g, 9.02 mmol) was dissolved in water (20 mL) and applied to a column of 65 mL of Amberlite IA-400 (OH⁻form) anion exchange resin. The column was washed with water. Basic fractions were combined and evaporated to a residual oil which was dried by evaporation of absolute ethanol and then at 0.5 mm to give (1S,4R)-4-amino-2-cyclopentene-1-methanol (1.2 g) as a pale yellow oil (darkens rapidly in air) which was used immediately. This oil was dissolved in ethanol (5 mL) and added to a solution of N-(4,6-dichloro-5-formamido-2-pyrimidinyl)acetamide (2.07 g, 8.31 mmol), prepared as described in Example 25, and triethylamine (2.50 g, 24.8 mmol). The resulting dark solution was heated (oil bath 75°–80° C.) under nitrogen for 50 minutes. The solution was evaporated to a syrup which was applied to a silica gel column. Title compound was eluted with 3 to 5% methanol-chloroform as a pale yellow solid foam (1.59 g, 54%); ¹H-NMR identical with that of crystallized sample. Such a sample was crystallized from ethanol to give white granules, m.p. 194°–195° C.; ¹H-NMR (DMSO-d₆) identical with that of the title compound of Example 25; $[\alpha]^{20}_D$ +2.7°, $[\alpha]^{20}_{578}$ +3.6°, $[\alpha]^{20}_{546}$ +2.9°, $[\alpha]^{20}_{436}$ −2.5°, $[\alpha]^{20}_{365}$ −41.2°.

EXAMPLE 28

(−)-(1S,4R)-cis-(2-Amino-6-chloro-9H-purin-9-yl)-2-cycylopentene-1-methanol

Title compound of Example 27 (1.15 g, 3.53 mmol) was gently refluxed in diethoxylmethyl acetate (45 mL) under nitrogen for 3.5 hours. The resulting pale yellow solution was concentrated at 0.5 mm Hg to a yellow syrup. The syrup was stirred in 1N HCl (50 mL) for 1.0 hour. This solution was neutralized with sodium bicarbonate and evaporated to dryness. The residual solids were extracted with methanol and the methanol-soluble material applied to a silica gel column. Elution of the column with 10% methanol-ethyl acetate gave title compound as a pale yellow solid foam (730 mg, 78%); $^1$H-NMR (DMSO-d$_6$): identical with that of racemate (title compound of Example 4); $[\alpha]^{20}_D$ −114.9° (c=0.26, MeOH).

EXAMPLE 29

(−)-(1S,4R)-cis-4-[2-Amino-6-(cyclopropylamino)-9H-purin-9-yl]-2-cyclopentene-1-methanol Title compound of Example 28 (560 mg, 2.11 mmol) in methanol (12 mL) was heated with cyclopropylamine (2.4 mL) in a Parr bomb at 78° C. for 17 hours. The solvent was evaporated and the residue chromatographed on silica gel. Title compound was eluted with 5–7% methanol-ethyl acetate as a colorless solid foam (367 mg, 59%); $^1$H-NMR (DMSO-d$_6$) identical with that of Example 17; $[\alpha]^{20}_D$ −59.0° (c=0.28, MeOH) confirms the absolute configuration of the title compound of Example 17.

EXAMPLE 30

(1S,4R)-4-Amino-2-cyclopentene-1-methanol dibenzoyl-D-tartrate

2-Azabicyclo[2.2.1]hept-5-en-3-one [Daluge and Vince, *J. Org. Chem.* 1978, 43, 2311 and U.S. Pat. No. 4,268,672] (44.0 g, 0.400 mole) was stirred in 2N HCl in methanol (0.5 L) at 25° C. for 1.5 hours. Volatiles were evaporated to leave (±)-cis-methyl-4-amino-2-cyclopentene-1-carboxylate hydrochloride as an off-white powder (71.1 g). Trituration of such a sample with diethylether gave white powder, m.p.92.5°–95° C. [*J. Org. Chem.* 1981, 46, 3271; m.p. 82°–83° C.]; $^1$H-NMR (DMSO-d$_6$) δ 8.25 (br s, 3, NH$_3^+$), 6.1 and 5.9 (both m, 2, CH=CH), 3.64 (s) overlapping 3.75–3.6 (m, total 4, OMe and CH), 2.65–2.45 and 2.05–1.85 (both m, 2, CH$_2$).

Anal. Calcd for C$_7$H$_{11}$NO$_2$.HCl: C, 47.33; H, 6.81; N, 7.89; Cl, 19.96. Found: C, 47.41; H, 6.84; N, 7.85; Cl, 19.89.

(±)-cis-Methyl-4-amino-2-cyclopentene-1-carboxylate hydrochloride (17.7 g, 0.100 mole) and diisobutylaluminum hydride (0.500 mole as a 1M solution in hexane) were refluxed in hexane (200 mL) for 6 hours. The resulting solution was cooled and 10 mL of 1M aqueous ammonium chloride and then methanol (200 mL) were added. This mixture was refluxed for 30 minutes and MgSO$_4$ (10 g) added. Solids were filtered off and washed with additional methanol. The filtrate-wash was evaporated to a dark oil (15.5 g); $^1$H-NMR (DMSO-d$_6$) identical to that of (±)-4-amino-2-cyclopentene-1-methanol prepared as described in Example 23. Such a sample, after purification by chromatography on silica gel (EtOH:CHCl$_3$:NH$_4$OH/10:90:1) was crystallized to the salt with dibenzoyl-D-tartaric acid (title compound of Example 23).

EXAMPLE 31

(−)-(1S,4R)-cis-(2-Amino-6-chloro-9H-purin-9-yl)-2-cyclopentene-1-methanol

A.

(±)-cis-4-(2,6-Diamino-9H-purin-9-yl)-2-cyclopentene-1-methanol (±)-(1α,4α)-4-(2-Amino-6-chloro-9H-purin-9-yl)-2-cyclopentene-1-methanol (1.50 g, 5.65 mmol) and ammonia (1, 35 ml) were stirred at 70° C. in a Parr bomb for 48 hours. Evaporation left crude product which was purified by elution from a silica gel column with 10% methanol-chloroform (1.27 g, 91%). Crystallization of such a sample from acetonitrile-methanol gave white granules, m.p. 145°–147° C.; $^1$H-NMR (Me$_2$SO-d$_6$) δ 7.59 (s, 1, purine H-8), 6.60 (br s, 2, NH$_2$), 6.09 and 5.85 (both m, 2, CH=CH), 5.71 (br s, 2, NH$_2$), 5.36 (m, 1, CH-N), 4.71 (t, J=5.4, 1, OH), 3.50–3.35 (m, 2, CH$_2$-O), 2.85 (m, 1, H-1'), 2.60 and 1.57 (both m, 2, CH$_2$).

Anal. Calcd. C$_{11}$H$_{14}$N$_6$O: C, 53.65; H, 5.73; N, 34.13 Found: C, 53.79; H, 5.79; N, 34.00.

B.

(1R,4S)-9-(4-Hydroxymethyl-2-cylcopentenyl)guanine (±)-cis-4-(2,6-Diamino-9H-purin-9-yl)-2-cyclopentene-1-methanol (1.26 g, 5.12 mmol) was dissolved in 514 mL of 0.02M potassium phosphate buffer (pH 7.4) with 16.4×10$^3$ units of calf intestinal adenosine deaminase (adenosine aminohydrolase EC 3.5.4.4 Boehringer Mannheim). After 6.5 hours at 25° C., the reaction was quenched by addition of a equal volume of methanol. The solution was evaporated to dryness and the residual solids extracted with hot methanol (4×100 ml). The contents of the methanol extracts was adsorbed on silica gel and loaded on a silica gel column packed in 10% MeOH-CHCl$_3$. Elution with 10% MeOH-CHCl$_3$ (400 ml) gave unreacted starting material (0.66 g). Crystallization from methanol-acetonitrile gave white granules of (+)-cis-4-(2,6-diamino-9H-purin-9-yl)-2-cyclopentene-1-methanol (0.38 g); m.p. 175°–178° C.; $^1$H-NMR (Me$_2$SO-d$_6$) identical with that of starting material; $[\alpha]^{20}$D +85.1° (c=0.19 in methanol). Continued elution of the column with 20–25% methanol chloroform (300 mL) gave, on evaporation, a white powder (0.62 g). Recrystallization from water gave title compound as white needles (0.56 g, 84%); m.p. >320° C.; $^1$H-NMR (Me$_2$SO-d$_6$) δ 10.54 (br s, 1, NHC=O), 7.59 (s, 1, H-8), 6.43 (br s, 2, NH$_2$), 6.1 and 5.8 (both m, 2, CH=CH), 5.3 (m, 1, CH-N), 4.73 (t, J=5.3, 1, OH), 3.43 (t, J=5.6, 2, CH$_2$-O), 2 8–2.6 (m, 1, H-4'), 2.65–2.55 and 1.60–1.50 (both m, 2, CH$_2$); $[\alpha]^{20}_D$ −96.3° (c=0.11 in 0.01N NaOH:MeOH/2:3); $[\alpha]^{20}_D$ −63.9°, (c=0.16, MeOH).

Anal. Calcd. C$_{11}$H$_{13}$N$_5$O$_2$·0.7 H$_2$O: C, 50.84; H, 5.59; N, 26.95. Found: C, 50.90; H, 5.63; N, 26.83.

C.

(1S,4R)-[4-(2-Amino-1,6-dihydro-6-oxo-9H-purin-9-yl)-2-cyclopenten-1-yl]methyl acetate (1R,4S)-9-(4-Hydroxymethyl-2-cyclopentenyl)guanine (150 mg, 0.607 mmole), acetic anhydride (freshly distilled, 65 mg, 0.161 mmole), 4-dimethylaminopyridine (3 mg), and dry dimethylformamide (5 mL) were stirred under nitrogen for days. The solvent was evaporated and the residue applied to a silica gel column. Title compound was eluted with 10% methanol-chloroform as a waxy white solid. Crystallization from ethanol gave white powder (123 mg, 70%), m.p. 247°–249° C.; $^1$H-NMR (DMSO-d$_6$) 10.55 (hr s, 1, NHCO), 7.55 (s, 1, purine H-8), 6.42 (br s, 2, NH$_2$), 6.06 and 5.94 (both m, 2, CH=CH), 5.34 (m, 1, CH—N), 4.07 (d, J=6.0, 2, CH$_2$O), 3.05 (m, 1, CH), 2.6 and 1.55 (both m, 2, CH$_2$), 1.98 (s, 3, COCH$_3$).

Anal. Calcd. for C$_{13}$H$_{15}$N$_5$O$_3$: C, 53.97; H, 5.23; N, 24.21. Found: C, 53.85; H, 5.25; N, 24.12.

D.

(−)-(1S,4R)-cis-(2-amino-6-chloro-9H-purin-9-yl)-2-cyclopentene-1-methanol (1S,4R)-[4-(2-Amino-1,6-dihydro-6-oxo-9H-purin-9-yl)-2-cyclopenten-1-yl]methyl acetate (50 mg, 0.17 mmole), phosphoryl chloride (2 mL), and N,N-diethyl aniline (38μL) were refluxed for 3 minutes. Volatiles were evaporated, and ice-water (5 mL) was added to the residual oil. The solution was neutralized and extracted with methylene chloride (3×20 mL). The methylene chloride layers were dried ($MgSO_4$) and evaporated to give crude product. Chromatography on silica gel (5% methanol-chloroform) gave (1S,4R)-[4-(2-amino-6-chloro-9H-purin-9-yl)-2-cyclopenten-1-yl]methyl acetate as pale yellow crystals from ethyl acetate, m.p. 124°-127°; $^1$H-NMR (DMSO-$d_6$) 8.01 (s, 1, purine H-8), 6.90 (s, 2, $NH_2$), 6.11 and 5.99 (both m, 2, CH=CH), 5.46 (m, 1, CH—N), 4.06 (d, J=6.2, 2, $CH_2O$), 3.1 (m, 1, CH—N), 2.7 and 1.65 (both m, 2, $CH_2$), 1.98 (s, 3, $CH_3CO$).

Deacetylation in ammonia-methanol provides the title compound of Example 28.

EXAMPLE 32

[cis-4-(2-Amino-6-(cyclopropylamino)-9H-purin-9-yl)-2-cyclopenten-1-yl]methyl R-2,3-bis-(hexadecanoyloxy)propyl hydrogen phosphate A solution of L-α-dipalmitoyl phosphatidyl choline (150 mg, 0.2 mmol, Sigma) in 6 mL of chloroform was added to a flask containing (±)-cis-4-(2-amino-6-(cyclopropylamino)-9H-purin-9-yl)-2-cyclopentene-1-methanol (300 mg, 1.03 mmol), phospholipase D, Type VII (from Streptomyces, 1.0 mg, specific activity 185 units/mg, Sigma) and pH 4.5 buffer (1.5 mL, 250 mM in $CaCl_2$, 200 mM in NaOAc adjusted to pH 4.5 by addition of 0.1N HCl). The resulting biphase was stirred at 45° C. (oil bath) for 1 hour. The layers were separated and the aqueous layer extracted with chloroform (3×6 mL). The combined organic layers were washed with 1N HCl, dried and concentrated. Such a sample was purified by elution from 2 silica gel columns with 12% methanol-chloroform to yield the title compound, 120 mg (47%). This material was solidified using ethylacetate-acetonitrile to produce a light yellow powder m.p 155°-157° C.; $^1$H-NMR ($CD_3CD-CDCl_3$) δ 7.78 (s, overlapping solvent, purine H-8), 6.12 and 5.88 (m, 2, HC=CH), 5.53 (m, 1, CHN cyclopentene), 5.22 (m, 1, $CO_2CH$), 4.37 (dd, J=3, 12; 1, ½$POCH_2$ glycerol), 4.12 (m, 1, ½ $POCH_2$ glycerol), 3.42 (m, 4, $OCH_2$ glycerol, $OCH_2$), 3.11 (br m, 1, CH), 2.90 (m, 1, NCH), 2.78 (m, 1, ½ $CH_2$ cyclopentene), 2.27 (m, 4, $2CH_2CO_2$), 1.70 (m, 1, ½ $CH_2$ cyclopentene), 1.56 (br m, 4, $2CH_2CH_2CO_2$), 1.27 (br m, 38, 24 $CH_2$), 0.88 (m, 6, $2CH_3$), 0.83 (m, 2, $CH_2$ cyclopropyl), 0.60 (m, 2, $CH_2$ cyclopropyl).

Anal. Calcd. for $C_{49}H_{85}N_6O_8P \cdot 2.4 H_2O$: C, 61.28; H, 9.42; N, 8.75; P, 3.22. Found: C, 60.97; H, 9.12N, 8.78; P, 2.96.

The preceding example is an adaptation of the procedure by Satoshi Shuto et al. Tetrahedron Letters, Vol. 28, No. 2, pp. 199-202, 1987.

EXAMPLE 33

[cis-4-(2-Amino-6-(cyclopropylamino)-9H-purin-9-yl)-2-cyclopenten-1-yl]methyl R-2,3-bis-(hexanoyloxy)propyl hydrogen phosphate A solution of L-α-dicaproyl phosphatidylcholine (300 mg, 0.66 mmol, Sigma) in 15 mL of $CHCl_3$ was added to a flask containing (±)-cis-4-((2-amino-6-(cyclopropylamino)-9H-purin-9-yl)-2-cyclopentene-1-methanol (378 mg, 1.32 mmol), phospholipase D, Type VII (from Streptomyces, 1.04 mg, specific activity 185 units/mg, Sigma), pH 4.5 buffer (4.5 mL, 250 mM in $CaCl_2$, 200 mM in NaOAc adjusted to pH 4.5 with HCl) and $CHCl_3$ (3 mL). The resulting biphase was stirred at 45° C. (oil bath) for 4 hours. The layers were separated and the organic layer washed with 1N HCl (2×4 mL). The combined aqueous layers were back washed with chloroform (10 mL). The combined organic layers were dried ($MgSO_4$) and concentrated. The residue was placed on a silica gel column and the title compound was eluted with 16% methanol-chloroform and concentrated to yield a fine yellow powder. This material was dissolved in ethanol and concentrated (3×50 mL) before drying under high vacuum to yield 103 mg (21% yield) of a light yellow powder, m.p. 182°-185° C.

$^1$H-NMR: (DMSO-$d_6$) δ 7.61 (s, 1, purine H8), 7.22 (br s, 1, NH), 6.09 (m, 1, ½ CH=CH), 5.89 (m, overlapping br s at 5.83, 3, ½ CH=CH, $NH_2$), 5.41 (br m, 1, CHN), 5.09 (br m, 1, $CO_2CH$), 4.30 (dd; J=2.7, 12; 1, ½ $POCH_2$ glycerol), 4.08 (m, 1, ½ $POCH_2$ glycerol), 3.80 (br m overlapping br m at 3.75, b, $OCH_2$ glycerol, $OCH_2$), 3.02 (br m, 2, CH, NCH cyclopropyl), 2.65 (m, 1, ½ $CH_2$ cyclopentene), 2.23 (+, J=7.5, 4, 2 $CH_2CO_2$), 1.48 (br m, 5, 2 $CH_2CH_2CO_2$, ½ $CH_2$ cyclopentene), 1.23 (br m, 8, 2 $(CH_2)_2$), 0.84 (m, 6, 2 $CH_3$), 0.67 and 0.58 (m, 4, 2 $CH_2$ cyclopropyl).

Calcd. for $C_{29}H_{45}N_6O_8P \cdot 3.9 H_2O$, 0.2 $CHCl_3$, 0.05 EtOH: C, 48.00; H, 7.33; N, 11.46; Cl, 2.9. Found: C, 48.65; H, 6.61; N, 10.81; Cl, 2.5.

The preceding example is an adaptation of the procedure by Satoshi Shuto et al. Tetrahedron Letters, Vol. 28, No. 2, pp. 199-202, 1987.

EXAMPLE A

Tablet Formulations

The following formulations A, B and C are prepared by wet granulation of the ingredients with a solution of povidone, followed by addition of magnesium stearate and compression.

| | Formulation A | mg/tablet | mg/tablet |
|---|---|---|---|
| (a) | Active ingredient | 250 | 250 |
| (b) | Lactose B.P. | 210 | 26 |
| (c) | Povidone B.P. | 15 | 9 |
| (d) | Sodium Starch Glycollate | 20 | 12 |
| (e) | Magnesium Stearate | 5 | 3 |
| | | 500 | 300 |

| | Formulation B | mg/tablet | mg/tablet |
|---|---|---|---|
| (a) | Active ingredient | 250 | 250 |
| (b) | Lactose | 150 | — |
| (c) | Avicel PH 101 | 60 | 26 |
| (d) | Povidone B.P. | 15 | 9 |

Formulation B -continued

|     |                        | mg/tablet | mg/tablet |
|-----|------------------------|-----------|-----------|
| (e) | Sodium Starch Glycollate | 20      | 12        |
| (f) | Magnesium Stearate       | 5       | 3         |
|     |                        | 500       | 300       |

Formulation C

|                     | mg/tablet |
|---------------------|-----------|
| Active ingredient   | 100       |
| Lactose             | 200       |
| Starch              | 50        |
| Povidone            | 5         |
| Magnesium stearate  | 4         |
|                     | 359       |

The following formulations, D and E, are prepared by direct compression of the admixed ingredients. The lactose in formulation E is of the direct compression type (Dairy Crest-"Zeparox").

Formulation D

|                           | mg/tablet |
|---------------------------|-----------|
| Active ingredient         | 250       |
| Pregelatinised Starch NF15| 150       |
|                           | 400       |

Formulation E

|                   | mg/tablet |
|-------------------|-----------|
| Active ingredient | 250       |
| Lactose           | 150       |
| Avicel            | 100       |
|                   | 500       |

Formulation F

Controlled Release Formulation

The formulation is prepared by wet granulation of the ingredients (below) with a solution of povidone followed by the addition of magnesium stearate and compression.

|     |                                               | mg/tablet |
|-----|-----------------------------------------------|-----------|
| (a) | Active ingredient                             | 500       |
| (b) | Hydroxypropylmethylcellulose (Methocel K4M Premium) | 112 |
| (c) | Lactose B.P.                                  | 53        |
| (d) | Povidone B.P.                                 | 28        |
| (e) | Magnesium Stearate                            | 7         |
|     |                                               | 700       |

Drug release takes place over a period of about 6-8 hours and is complete after 12 hours.

EXAMPLE B

Capsule Formulations

Formulation A

A capsule formulation is prepared by admixing the ingredients of Formulation D in Example A above and filling into a two-part hard gelatin capsule. Formulation B (infra) is prepared in a similar manner.

Formulation B

|     |                          | mg/capsule |
|-----|--------------------------|------------|
| (a) | Active ingredient        | 250        |
| (b) | Lactose B.P.             | 143        |
| (c) | Sodium Starch Glycollate | 25         |
| (d) | Magnesium Stearate       | 2          |
|     |                          | 420        |

Formulation C

|     |                    | mg/capsule |
|-----|--------------------|------------|
| (a) | Active ingredient  | 250        |
| (b) | Macrogol 4000 B.P. | 350        |
|     |                    | 600        |

Capsules of formulation C are prepared by melting the Macrogol 4000 BP, dispersing the active ingredient in the melt and filling the melt into a two-part hard gelatin capsule.

Formulation D

|                   | mg/capsule |
|-------------------|------------|
| Active ingredient | 250        |
| Lecithin          | 100        |
| Arachis Oil       | 100        |
|                   | 450        |

Capsules of formulation D are prepared by dispersing the active ingredient in the lecithin and arachis oil and filling the dispersion into soft, elastic gelatin capsules.

Formulation E

Controlled Release Capsule

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|     |                          | mg/capsule |
|-----|--------------------------|------------|
| (a) | Active ingredient        | 250        |
| (b) | Microcrystalline Cellulose | 125      |
| (c) | Lactose B.P.             | 125        |
| (d) | Ethyl Cellulose          | 13         |
|     |                          | 513        |

EXAMPLE C

Injectable Formulation

Formulation A.

|                                                | |
|------------------------------------------------|-|
| Active ingredient                              | 0.200 g |
| Hydrochloric acid solution, 0.1M, or           | 4.0 to 7.0 |
| Sodium hydroxide solution, 0.1M q.s. to pH     | |
| Sterile water q.s. to                          | 10 ml |

The active ingredient is dissolved in most of the water (35°-40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B. | |
|---|---|
| Active ingredient | 0.125 g |
| Sterile, pyrogen-free, pH 7 phosphate buffer q.s. to | 25 ml |

EXAMPLE D

| Intramuscular injection | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE E

| Syrup | |
|---|---|
| Active ingredient | 0.25 g |
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE F

| Suppository | |
|---|---|
| | mg/suppository |
| Active ingredient (631 m)* | 250 |
| Hard Fat, BP (Witepsol H15 - Dynamit NoBel) | 1770 |
| | 2020 |

*The active ingredient is used as a powder wherein at least 90% of the particles are of 631 m diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogeneous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE G

| Pessaries | |
|---|---|
| | mg/pessary |
| Active ingredient (631 m) | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture

Antiviral Activity

The compound of Example 5 was tested for anti-HIV activity in MT4 cells according to the method described by Averett, D. R., *J. Virol. Methods,* 23 1989, 263–276 and was found to have an $IC_{50}$ value of $21\pm12$ $\mu$M (13 determinations). The $IC_{50}$ value of the compound of Example 17 was 3.6 $\mu$M (an average of two determinations).

I claim:

1. A method of treatment of a viral infection in a mammal which comprises administering to said mammal an effective antiviral amount of a compound of formula I:

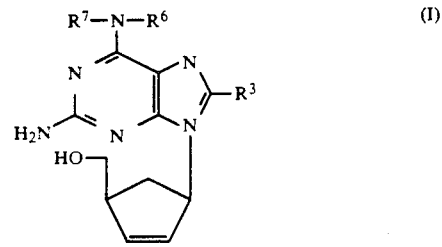

wherein $R^3$ represents hydrogen or $C_{1-6}$ alkyl; $R^6$ represents $C_{3-8}$ cycloalkyl, and $R^7$ represents a hydrogen atom or a branched or straight chain $C_{1-6}$ alkyl; or a pharmaceutically acceptable ester or a pharmaceutically acceptable salt thereof.

2. The method according to claim 1 for the treatment of an HIV infections.

3. A method according to claim 1 for the treatment of a hepatitis B infection.

4. A method according to claim 2 wherein the antiviral compound is (−)-cis-4-[2-amino-6-(cyclopropylamino)-9H-purin-9-yl]-2-cyclopentene-1-methanol or racemic or partially resolved mixtures with the (+)-cis enantiomer thereof.

5. A method according to claim 3 wherein the antiviral compound is (−)-cis-4-[2-amino-6-(cyclopropylamino)-9H-purin-9-yl]-2-cyclopentene-1-methanol or racemic or partially resolved mixtures with the (+)-cis enantiomer thereof.

6. A method according to claim 1 comprising administering to said mammal 15 to 60 mg/kg of body weight per day of a compound of formula I or a pharmaceutically acceptable salt or a pharmaceutically acceptable ester thereof.

7. A method according to claim 6 in which the infection is an HIV infection and the mammal is a human.

8. A method according to claim 6 in which the infection is a hepatitis B infection and the mammal is a human.

9. A method of treating an HIV infection in a mammal which comprises administering to said mammal an effective anti-HIV amount of (—)-cis-4-{2-amino-6-(cyclopropylamino)-9H-purin-9-yl}-2-cyclopentene-1-methanol or racemic or partially resolved mixtures thereof with the (+)-cis-enantiomer or a pharmaceutically acceptable ester or a pharmaceutically acceptable salt thereof.

10. A method of treating an HIV infection in a mammal which comprises administering to said mammal an effective anti-HIV amount of (—)-cis-4-{2-amino-6-(cyclopropylmethylamino)-9H-purin-9-yl{-2-cyclopentene-1-methanol or racemic or partially resolved mixtures thereof with the (+)-cis-enantiomer or a pharmaceutically acceptable ester or a pharmaceutically acceptable salt thereof.

11. A method according to claim 9 or 10, in which the pharmaceutically acceptable ester is a mono-, di- or triphosphate.

12. A method according to claim 9 or 10, in which the pharmaceutically acceptable salt is hydrochloride.

13. A method according to claim 9 or 10, in which the mammal is a human.

14. A method of treating an HIV infection in a mammal which comprise administering to said mammal an effective anti-HIV amount of (—)-cis-4-{2-amino-6-(cyclopropylamino)-9H-purin-9-yl}-2-cyclopentene-1-methanol or racemic or partially resolved mixtures thereof with the (+)-cis-enantiomer or a pharmaceutically acceptable ester or a pharmaceutically acceptable salt thereof.

15. A method of treating an HIV infection in a mammal which comprises administering to said mammal an effective anti-HIV amount of (—)-cis-b 4-{2-amino-6-(cyclopropylmethylamino)-9H-purin-9-yl}-2-cyclopentene-1-methanol or racemic or partially resolved mixtures thereof with the (+)-cis-enantiomer or a pharmaceutically acceptable ester or a pharmaceutically acceptable salt thereof.

16. A method according to claim 14 or 15, in which the pharmaceutically acceptable ester is a mono-, di- or tri-phosphate.

17. A method according to claim 14 or 15, in which the mammal is a human.

* * * * *